United States Patent [19]

Clements-Jewery et al.

[11] Patent Number: 4,751,233
[45] Date of Patent: Jun. 14, 1988

[54] 8[2-(IMIDAZOLYL)THIO] AND 8[2-(THIAZOLYL)THIO]-5,6,7,8-TETRAHYDROQUINOLINES, AND ANTI-ALLERGIC USE THEREOF

[75] Inventors: Stephen Clements-Jewery; Peter D. Kennewell, both of Swindon; Robert Westwood, Faringdon, all of United Kingdom

[73] Assignee: Roussel Uclaf, Paris, France

[21] Appl. No.: 833,853

[22] Filed: Feb. 26, 1986

[30] Foreign Application Priority Data

Mar. 4, 1985 [GB] United Kingdom ............... 8505492

[51] Int. Cl.⁴ ............... C07D 403/14; C07D 417/12; A61K 31/415; A61K 31/425
[52] U.S. Cl. ............... 514/314; 546/176; 546/177; 546/178
[58] Field of Search ............... 546/178, 167, 177; 514/314

[56] References Cited

U.S. PATENT DOCUMENTS 3,857,877 12/1974 Somasekhara ............... 546/177
3,991,060 11/1976 Curran et al. ............... 546/177

FOREIGN PATENT DOCUMENTS 1503697 10/1967 France ............... 546/177
1463582 2/1977 United Kingdom ............... 546/171
243618 3/1967 U.S.S.R. ............... 546/167

Primary Examiner—Glennon H. Hollrah
Assistant Examiner—D. B. Springer
Attorney, Agent, or Firm—Bierman and Muserlian

[57] ABSTRACT

Novel 8-thiotetrahydroquinolines of the formula

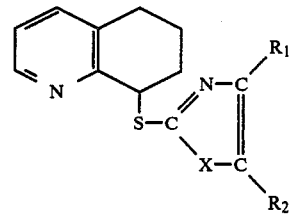

I wherein X is selected from the group consisting of

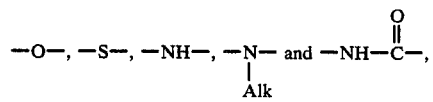

Alk is alkyl of 1 to 6 carbon atoms, $R_1$ and $R_2$ are Alk individually selected from the group consisting of hydrogen and aryl or taken together with the carbon atoms to which they are attached form a phenyl optionally substituted with at least one member of the group consisting of alkyl, alkoxy and alkylthio of 1 to 6 carbon atoms, halogen,

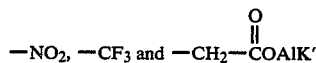

and Alk' is alkyl of 1 to 6 carbon atoms and their non-toxic, pharmaceutically acceptable acid addition salts having antiallergic activity and their preparation.

12 Claims, No Drawings

8[2-(IMIDAZOLYL)THIO] AND 8[2-(THIAZOLYL)THIO]-5,6,7,8-TETRAHYDROQUINOLINES, AND ANTI-ALLERGIC USE THEREOF

OBJECTS OF THE INVENTION

It is an object of the invention to provide the novel 8-thiotetrahydroquinolines of formula I and a novel process for their preparation.

It is another object of the invention to provide novel antiallergic compositions and a novel method of combatting allergic conditions in warm-blooded animals.

These and other objects and advantages of the invention will become obvious from the following detailed description.

THE INVENTION

The novel compounds of the invention are selected from the group consisting of 8-thiotetrahydroquinolines of the formula

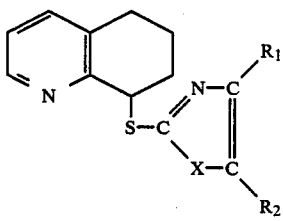

I wherein X is selected from the group consisting of

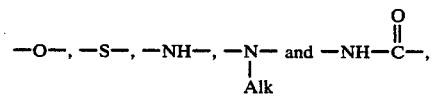

Alk is alkyl of 1 to 6 carbon atoms, $R_1$ and $R_2$ are individually selected from the group consisting of hydrogen and aryl or taken together with the carbon atoms to which they are attached form a phenyl optionally substituted with at least one member of the group consisting of alkyl, alkoxy and alkylthio of 1 to 6 carbon atoms, halogen,

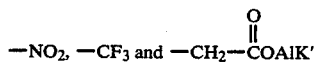

and Alk' is alkyl of 1 to 6 carbon atoms and their non-toxic, pharmaceutically acceptable acid addition salts.

Examples of aryl for $R_1$ and $R_2$ are phenyl and naphthyl and examples of alkyl, alkoxy and alkylthio of 1 to 6 carbon atoms include methyl, ethyl, n-propyl, isopropyl and branched and straight chain butyl, pentyl and hexyl, methoxy, ethoxy, n-propoxy, isopropoxy, branched and straight chain butoxy, pentyloxy and hexyloxy, methylthio, n-propylthio, isopropylthio and straight and branched chain butylthio, pentylthio and hexylthio. Examples of suitable halogens are chlorine and bromine.

Examples of suitable acids for the formation of the non-toxic, pharmaceutically acceptable acid addition salts are mineral acids such as hydrochloric acid, hydrobromic acid, hydroiodic acid, nitric acid, sulfuric acid and phosphoric acid and organic acids such as formic acid, propionic acid, benzoic acid, maleic acid, fumaric acid, succinic acid, tartaric acid, citric acid, oxalic acid, glyoxylic acid, aspartic acid, alkanesulfonic acids such as methanesulfonic acid and arylsulfonic acids such as benzenesulfonic acid.

Among the preferred compounds of formula I are those wherein $R_1$ and $R_2$ together with the carbon atoms to which they are attached form a phenyl optionally substituted with at least one member of the group consisting of alkyl, alkoxy and alkylthio of 1 to 4 carbon atoms, halogen, $-NO_2$, $-CF_3$, $-CH_2COOCH_3$ and $-CH_2COOCH_2-CH_3$ and those wherein X is $-S-$ or $-NH-$ and their non-toxic, pharmaceutically acceptable acid addition salts.

Among preferred specific compounds of formula I are 8-(2-benzothiazolylthio)-5,6,7,8-tetrahydroquinoline; 8-(6-chloro-1H-benzimidazol-2-ylthio)-5,6,7,8-tetrahydroquinoline; 8-[(5-chloro-2-benzothiazolyl)thio]-5,6,7,8-tetrahydroquinoline; 8-[(6-chloro-2-benzothiazolyl)thio]-5,6,7,8-tetrahydroquinoline; 8-[(6-ethoxy-2-benzothiazolyl)thio]-5,6,7,8-tetrahydroquinoline; 8-[(6-ethylthio-2-benzothiazolyl)thio]-5,6,7,8-tetrahydroquinoline: 8-[(6-nitro-2-benzothiazolyl)thio]-5,6,7,8-tetrahydroquinoline; and 8-(4,5-diphenyl-1H-imidazol-2-ylthio)-5,6,7,8-tetrahydroquinoline, and their non-toxic, pharmaceutically acceptable acid addition salts thereof.

The novel process of the invention for the preparation of the compounds of formula I comprises reacting a salt of a compound of the formula

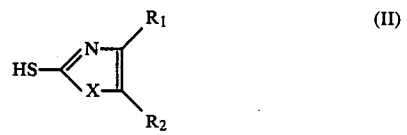

(II)

wherein X, $R_1$ and $R_2$ are as defined above with a compound of the formula

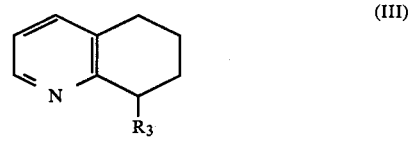

(III)

wherein $R_3$ is halogen, e.g. a chlorine, bromine or iodine atom and, if desired, subsequent salification of the compound of formula I.

The reaction is preferably carried out in the presence of an organic solvent such as ether or tetrahydrofuran.

The salt of a compound of formula II may be obtained by reaction of a compound of formula II with a reagent capable of forming an anion thereof. Such an anion-forming reagent is preferably an alkali metal hydride, e.g. sodium hydride.

The compounds of formula I of the invention are basic in character and may subsequently, if desired, be converted into the acid addition salts thereof, particularly the physiologically acceptable acid addition salts thereof with inorganic or organic acids, for example by conventional methods such as by reacting the compounds as bases with a solution of a stoichiometric amount of the corresponding acid in a suitable solvent. Such salts may be prepared in situ in the reaction mixture without the necessity for intermediate isolation of the free bases themselves. Conversely, the acid addition salts of the compounds of formula I obtained may, if desired, subsequently be converted into compounds of formula I or into further acid addition salts thereof.

The antiallergic compositions of the invention are comprised of an antiallergically effective amount of at least one compound of formula I and their non-toxic, pharmaceutically acceptable acid addition salts and an inert pharmaceutical carrier or excipient. The compositions may be in the form of tablets, dragees, capsules, gelatin capsules, powders, suppositories, aerosols and injectable solutions or suspensions.

Examples of suitable excipients are talc, arabic gum, lactose, starch, magnesium stearate, cocoa butter, aqueous and nonaqueous vehicles, animal and vegetable fats, paraffin derivatives, glycols, various wetting dispersing and emulsifying agents and preservatives.

The compositions have a remarkable activity towards inhibition of 5-lipoxygenase and of binding of leukotriene $D_4$ to its receptors making them useful as antialergic compositions. The compositions are useful for the treatment of allergic asthmatic conditions and bronchitis having allergic origins Among the preferred compositions of the invention are those wherein X is —S— or —NH— and those wherein $R_1$ and $R_2$ together with the carbon atoms to which they are attached form phenyl optionally substituted with at least one member of the group consisting of alkyl, alkoxy and alkylthio of 1 to 4 carbon atoms, halogen, -$NO_2$, —$CF_3$, —$CH_2COOCH_3$ and —$CH_2COOCH_2$—$CH_3$ and their non-toxic, pharmaceutically acceptable acid addition salts.

Among the preferred compositions of the invention are those wherein the active compound is selected from the group consisting of 8-[2-benzothiazolylthio)-5,6,7,8-tetrahydroquinoline; 8-(6-chloro-1H-benzimidazol-2-ylthio)-5,6,7,8-tetrahydroquinoline; 8-[(5-chloro-2-benzothiazolyl)thio]-5,6,7,8-tetrahydroquinoline; 8-[(6-chloro-2-benzothiazolyl)thio]-5,6,7,8-tetrahydroquinoline; 8-[(6-ethoxy-2-benzothiazolyl)thio]-5,6,7,8-tetrahydroquinoline; 8-[(6-ethylthio-2-benzothiazolyl)thio]-5,6,7,8-tetrahydroquinoline; 8-[(6-nitro-2-benzothiazolyl)thio]-5,6,7,8-tetrahydroquinoline; and 8-(4,5-diphenyl-1H-imidazol-2-ylthio)-5,6,7,8-tetrahydroquinoline, and their non-toxic, pharmaceutically acceptable acid addition salts thereof.

The novel method of the invention for combatting allergies in warm-blooded animals, including humans, comprises administering to warm-blooded animals an antiallergically effective amount of at least one compound of formula I and their non-toxic, pharmaceutically acceptable acid addition salts. The compounds may be administered orally, rectally or parenterally and the usual daily dose is 0.0015 to 2.75 mg/kg depending on the condition treated, the specific compound and the method of administration.

In the following examples there are described several preferred embodiments to illustrate the invention. However, it should be understood that the invention is not intended to be limited to the specific embodiments.

EXAMPLE 1

8-(2-benzothiazolylthio)-5,6,7,8-tetrahydroquinoline 2.0 g (66.67 mmol) of 80% sodium hydride in oil were added to 9.97 g (59.1 mmol) of 2-mercaptobenzothiazole in 250 ml of dry tetrahydrofuran under nitrogen. The suspension was stirred at ambient temperature and, when effervescence had ceased 10 g (59.65 mmol) of 8-chloro-5,6,7,8-tetrahydroquinoline were added via a syringe. The reaction mixture was stirred at ambient temperature for 48 hours and the solvent was removed under reduced pressure. The residue was partitioned between water and dichloromethane and the organic phase was washed with water, dried over $MgSO_4$ and concentrated to dryness under reduced pressure. The resulting oil was purified by flash column chromatography over silica (75 g)with elution with a mixture of dichloromethane and diethyl ether (1:0 gradually changing to 0:1). The pale yellow oil residue was crystallized from a mixture of dichloromethane-40°–60° petroleum ether to obtain 10.9 g (61%) of 8-(2-benzothiazolylthio)-5,6,7,8-tetrahydroquinoline in form of white crystals melting at 72°–3° C.

NMR Spectrum ($CDCl_3$)

$\delta_H$: 1.95 (1H, mult.), 2.15 (1H, mult.), 2.48 (2H, mult.), 2.84 (2H, mult.), 5.50 (1H, triplet, J =5Hz), 7.14 (1H, mult.), 7.38 (3H, mult.), 7.76 (1H, mult.), 7.91 (1H, mult.) and 8.49 (1H, mult.)

Analysis: $C_{16}H_{14}N_2S_2$ Calculated: % C 64.39; % H 4.74; % N 9.38; % S 21.49; Found: % C 64.45; % H 4.81; % N 9.35; % S 21.20.

EXAMPLES 2 to 27

Using the method of Example 1, but starting from the corresponding compounds of formula II, the compounds of Examples 2 to 27 were prepared and the yield, melting point and analytical data are given in Table I.

Example 2: 8-(6-methoxy-1H-benzimidazol-2-ylthio)-5,6,7,8-tetrahydroquinoline.

Example 3: 8-(1H-benzimidazol-2-ylthio)-5,6,7,8-tetrahydroquinoline.

Example 4: ethyl 2-[(5,6,7,8-tetrahydro-8-quinolinyl)-thio]-1H-benzimidazole-5-acetate.

Example 5: 8-(6-nitro-1H-benzimidazol-2-ylthio)-5,6,7,8-tetrahydroquinoline.

Example 6: 8-(6-methyl-1H-benzimidazol-2-ylthio)-5,6,7,8-tetrahydroquinoline.

Example 7: 8-(5,6-dichloro-1H-benzimidazol-2-ylthio)-5,6,7,8-tetrahydroquinoline.

Example 8: 8-(6-chloro-1H-benzimidazol-2-ylthio)-5,6,7,8-tetrahydroquinoline.

Example 9: 8-(2-benzoxazolylthio)-5,6,7,8-tetrahydroquinoline.

Example 10: methyl 2-[(5,6,7,8-tetrahydro-8-quinolinyl)-thio]benzoxazole-5-acetate.

Example 11: 8-[(5-chloro-2-benzothiazolyl)thio]-5,6,7,8-tetrahydroquinoline.

Example 12: 8-[(6-chloro-2-benzothiazolyl)thio-5,6,7-8-tetrahydroquinoline.

Example 13: 8-[(6-ethoxy-2-benzothiazolyl)thio]-5,6,7,8-tetrahydroquinoline.

Example 14: 2-[(5,6,7,8-tetrahydroquinoline-8-yl)thio]-4(3H)-quinazolinone.

Example 15: 8-[(6-methyl-2-benzothiazolyl)thio]-5,6,7,8-tetrahydroquinoline.

Example 16: 8-[(5-nitro-2-benzothiazolyl)thio]-5,6,7,8-tetrahydroquinoline.

Example 17: 8-[(5-methyl-2-benzothiazolyl)thio]-5,6,7,8-tetrahydroquinoline.

Example 18: 8-[(5,6-dichloro-2-benzothiazolyl)thio]-5,6,7,8-tetrahydroquinoline.

Example 19: 8-[(6-ethylthio-2-benzothiazolyl)thio]-5,6,7,8-tetrahydroquinoline.

Example 20: 8-(6-nitro-2-benzothiazolyl)thio]-5,6,7,8-tetrahydroquinoline.
Example 21: 8-[(5-trifluoromethyl-2-benzothiazolyl)thio]-5,6,7,8- tetrahydroquinoline.
Example 22: 8-[(4,6-dichloro-2-benzothiazolyl)thio]-5,6,7,8-tetrahydroquinoline.
Example 23: 8-(4-chloro-2-benzothiazolyl)thio]-5,6,7,8-tetrahydroquinoline.
Example 24: 8-[(4-methyl-2-benzothiazolyl)thio]-5,6,7,8-tetrahydroquinoline.
Example 25: 8-(4,5-diphenyl-1H-imidazol-2-ylthio)-5,6,7,8-tetrahydroquinoline.
Example 26: 8-(1-methylimidazol-2-ylthio)-5,6,7,8-tetrahydroquinoline.
Example 27: 8-(2-thiazolylthio)-5,6,7,8-tetrahydroquinoline.

TABLE I

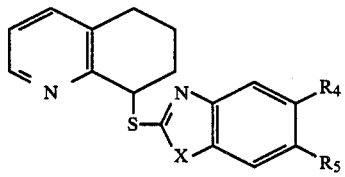

| Example | $R_1$ | $R_2$ | $R_4$ | $R_5$ | $R_6$ | X | Yield (%) | M.p. (°C.) | Formula | C | H | N | S | Cl |
|---|---|---|---|---|---|---|---|---|---|---|---|---|---|---|
| 1 |  |  | H | H |  | S | 61 | 73 | $C_{16}H_{14}N_2S_2$ | 64.39 | 4.74 | 9.38 | 21.49 |  |
|  |  |  |  |  |  |  |  |  |  | 64.45 | 4.81 | 9.35 | 21.20 |  |
| 2 |  |  | H | OMe |  | NH | 31 | 159–161 | $C_{17}H_{17}N_3OS.2HCl$ 1.5H$_2$O | 49.64 | 5.39 | 10.22 | 7.79 | 17.24 |
|  |  |  |  |  |  |  |  |  |  | 49.36 | 5.38 | 10.16 | 7.85 | 17.41 |
| 3 |  |  | H | H |  | NH | 55 | 195 | $C_{16}H_{15}N_3S.2HCl$ | 54.24 | 4.85 | 11.85 | 9.05 | 20.01 |
|  |  |  |  |  |  |  |  |  |  | 54.02 | 4.85 | 11.84 | 9.18 | 20.22 |
| 4 |  |  | CH$_2$CO$_2$Et | H |  | NH | 29 | 110–111 | $C_{20}H_{21}N_3O_2S.2HCl$ | Not available | | | | — |
| 5 |  |  | H | NO$_2$ |  | NH | 74 | 109–110 | $C_{16}H_{14}N_4O_2S.H_2O$ | 55.80 | 4.68 | 16.27 | 9.31 | — |
|  |  |  |  |  |  |  |  |  |  | 55.74 | 4.71 | 16.29 | 9.31 | — |
| 6 |  |  | H | CH$_3$ |  | NH | 49 | 178 | $C_{17}H_{17}N_3S.2HCl$ | 55.43 | 5.21 | 11.40 | 8.70 | 19.25 |
|  |  |  |  |  |  |  |  |  |  | 55.18 | 5.31 | 11.17 | 8.60 | 19.12 |
| 7 |  |  | Cl | Cl |  | NH | 45 | 105–6 | $C_{16}H_{13}N_3Cl_2S.H_2O$ | 52.18 | 4.11 | 11.41 | 8.74 | 19.25 |
|  |  |  |  |  |  |  |  |  |  | 52.26 | 4.17 | 11.45 | 8.74 | 19.27 |
| 8 |  |  | H | Cl |  | NH | 44 | 162–66 | $C_{16}H_{14}N_3ClS.2HCl$ | 49.43 | 4.16 | 10.80 | 8.25 | 27.36 |
|  |  |  |  |  |  |  |  |  |  | 49.25 | 4.24 | 10.65 | 8.26 | 27.25 |
| 9 |  |  | H | H |  | O | 48 | 68–71 | $C_{16}H_{14}N_2OS$ | 68.05 | 5.01 | 9.92 | 11.35 | — |
|  |  |  |  |  |  |  |  |  |  | 67.50 | 5.03 | 9.89 | 11.39 | — |
| 10 |  |  | CH$_2$CO$_2$Me | H |  | O | 25 | 87–88 | $C_{19}H_{18}N_2O_3S$ | 64.38 | 5.13 | 7.90 | 9.05 | — |
|  |  |  |  |  |  |  |  |  |  | 64.28 | 5.15 | 7.93 | 9.17 | — |
| 11 |  |  | Cl | H |  | S | 61 | 155–156 | $C_{16}H_{13}N_2ClS_2.HCl$ | 52.03 | 3.83 | 7.58 | 17.36 | 19.20 |
|  |  |  |  |  |  |  |  |  |  | 51.80 | 3.95 | 7.52 | 17.00 | 19.67 |
| 12 |  |  | H | Cl |  | S | 82 | 169 | $C_{16}H_{13}N_2ClS_2.3HCl$ | 52.03 | 3.83 | 7.58 | 17.36 | 19.20 |
|  |  |  |  |  |  |  |  |  |  | 52.02 | 3.88 | 7.64 | 17.22 | 19.45 |
| 13 |  |  | H | OEt |  | S | 71 | 156–8 | $C_{18}H_{18}N_2OS_2.HCl$ | 57.05 | 5.06 | 7.39 | 16.92 | 9.36 |
|  |  |  |  |  |  |  |  |  |  | 57.08 | 5.10 | 7.38 | 16.69 | 9.69 |
| 14 |  |  | H | H |  | NHCO | 45 | 192–3 | $C_{17}H_{15}N_3OS$ | 65.99 | 4.90 | 13.58 | 10.36 |  |
|  |  |  |  |  |  |  |  |  |  | 65.68 | 4.99 | 13.40 | 10.27 |  |
| 15 |  |  | H | Me |  | S | 56 | 162–4* | $C_{17}H_{16}N_2S_2.HCl$ | 58.52 | 4.92 | 8.02 |  |  |
|  |  |  |  |  |  |  |  |  |  | 58.23 | 5.05 | 7.82 |  |  |
| 16 |  | NO$_2$ |  | H |  | S | 43 | 130–1 | $C_{16}H_{13}N_3O_2S_2$ | 55.96 | 3.82 | 12.23 | 18.67 |  |
|  |  |  |  |  |  |  |  |  |  | 55.58 | 3.85 | 12.13 | 18.32 |  |
| 17 |  | Me |  | H |  | S | 18 | 155–7* | $C_{17}H_{16}N_2S_2.HCl$ | 58.52 | 4.92 | 8.02 |  | 10.16 |
|  |  |  |  |  |  |  |  |  |  | 58.31 | 4.94 | 8.01 |  | 10.33 |
| 18 |  |  | Cl | Cl |  | S | 30 | 165–7* | $C_{16}H_{12}N_2S_2Cl_2.HCl$ | 47.59 | 3.25 | 6.93 | 15.88 | 26.34 |
|  |  |  |  |  |  |  |  |  |  | 47.55 | 3.29 | 7.00 |  | 26.02 |
| 19 |  |  | H | SEt |  | S | 51 | 138–40* | $C_{18}H_{18}N_2S_3.HCl$ | 54.73 | 4.86 | 7.09 | 24.35 | 8.98 |
|  |  |  |  |  |  |  |  |  |  | 54.52 | 4.89 | 7.07 | 23.80 | 9.20 |

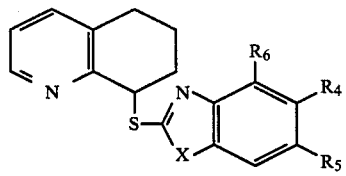

| Example | $R_1$ | $R_2$ | $R_4$ | $R_5$ | $R_6$ | X | Yield (%) | M.p. (°C.) | Formula | C | H | N | S | Cl |
|---|---|---|---|---|---|---|---|---|---|---|---|---|---|---|
| 20 |  |  | H | NO$_2$ | H | S | 30 | 161–2 | $C_{16}H_{13}N_3O_2S_2.HCl$ | 50.59 | 3.71 | 11.06 |  | 9.33 |
|  |  |  |  |  |  |  |  |  |  | 50.58 | 3.78 | 11.05 |  | 9.27 |
| 21 |  |  | CF$_3$ | H | H | S | 18 | 119–29 | $C_{17}H_{13}F_3N_2S_2.HCl$ | 50.68 | 3.50 | 6.95 |  | 8.80 |
|  |  |  |  |  |  |  |  |  |  | 50.62 | 3.55 | 6.89 |  | 8.70 |
| 22 |  |  | H | Cl | Cl | S | 15 | 158–61* | $C_{16}H_{12}N_2S_2Cl_2.HCl$ | 47.59 | 3.25 | 6.93 | 15.88 | 26.34 |
|  |  |  |  |  |  |  |  |  |  | 47.49 | 3.28 | 6.93 | 15.64 | 26.27 |
| 23 |  |  | H | H | Cl | S | 49 | 154–8 | $C_{16}H_{13}N_2S_2Cl.HCl$ | 52.03 | 3.82 | 7.58 |  | 19.20 |
|  |  |  |  |  |  |  |  |  |  | 52.06 | 3.91 | 7.55 |  | 19.29 |
| 24 |  |  | H | H | Me | S | 46 | 131–8 | $C_{17}H_{16}N_2S_2.HCl$ | 58.52 | 4.91 | 8.03 |  | 10.16 |
|  |  |  |  |  |  |  |  |  |  | 58.27 | 4.96 | 8.00 |  | 10.38 |

TABLE I-continued

| Example | R₁ | R₂ | R₄ | R₅ | R₆ | X | Yield (%) | M.p. (°C.) | Formula | Theory/Found (%) C | H | N | S | Cl |
|---|---|---|---|---|---|---|---|---|---|---|---|---|---|---|

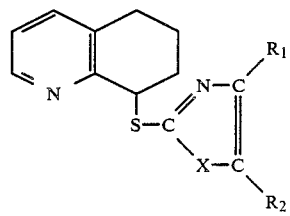

| 25 | Ph | Ph | | | | NH | 51 | 181–2 | C₂₄H₂₁N₃S.2HCl | 63.15 | 5.09 | 9.20 | 7.02 | 15.53 |
| | | | | | | | | | | 62.90 | 5.16 | 9.06 | 6.96 | 15.60 |
| 26 | H | H | | | | NMe | 42 | 178–9 | C₁₃H₁₅N₃S.2HCl.H₂O | 46.43 | 5.69 | 12.50 | 9.53 | 21.09 |
| | | | | | | | | | | 46.20 | 5.64 | 12.51 | 9.61 | 21.01 |
| 27 | H | H | | | | S | 41 | 118–20 | C₁₂H₁₂N₂S₂.2HCl ½EtOH | 45.20 | 4.80 | 8.32 | 19.05 | 21.06 |
| | | | | | | | | | | 44.57 | 4.88 | 8.21 | 19.65 | 20.67 |

° = decomposition

EXAMPLE 28

Tablets were prepared containing 20 mg of the compound of Example 11 or 13 and sufficient excipient of lactose, starch, talc and magnesium stearate for a final tablet weight of 100 mg.

A dosed aerosol was prepared delivering 2 mg of the compound of Example 1, 0.15 mg of emulsifier and 50 mg of propellant per dose.

PHARMACOLOGICAL DATA

A. 5-LIPOX

Inhibition of the Ca++ionophore (A23187) induced release of 5-lipoxygenase products, leukotriene B₄ and 5-HETE, from [¹⁴C]arachidonic acid pre-labelled rat peritoneal neutrophils. Assayed by a modification of the method reported by Ahnfelt-Ronne et al [Biochemical Pharmacology, Vol. 31, No. 16, pp 2616–2624 (1982)]. Data presented in Table II are micromolar concentrations of test compound causing 50% inhibition of control response determined graphically from dose-response curves.

B. LTD₄ RECEPTOR

Inhibition of the specific binding of [³H]-LTD₄ to a membrane preparation of guinea-pig lung tissue was assayed by a modification of a method reported by Bruns et al [Life Sciences, Vol. 33, pp. 645–653 (1983)]and the data presented in Table II are micromolar concentrations of the tested compound causing 50% ihibition of specific binding determined graphically from dose-response curves. The results of these tests are given in Table II.

TABLE II

| Example | 5-LIPOX | LTD₄ receptor | |
|---|---|---|---|
| 1 | 1.8 | 10 | |
| 2 | 58.0 | | |
| 3 | 35.1 | >100 | |
| 4 | 20.0 | | |
| 5 | 6.6 | >100 | |
| 6 | 5.0 | 74 | |
| 7 | 4.2 | | |
| 8 | 1.9 | 6.3 | |
| 9 | 16.9 | >100 | |
| 10 | 14.1 | 12 | |
| 11 | 1.5 | 100 | |
| 12 | 2.6 | 8.9 | |
| 13 | 1.2 | 9.0 | |
| 14 | >100 | >100 | |
| 15 | 2.3 | 9.5 | |
| 16 | 2.0 | >100 | |
| 17 | 1.5 | 7.1 | |
| 18 | 45 | 100 | |
| 19 | 1.1 | 1.7 | |
| 20 | 4.0 | >100 | |
| 21 | 2.6 | 18 | |
| 22 | 22 | >100 | |
| 23 | 12 | 33 | |
| 24 | 3.5 | 14 | |
| 25 | 3.0 | >100 | pot. |
| 26 | >100 | >100 | |
| 27 | 25.1 | >100 | |

Various modifications of the compounds and method of the invention may be made without departing from the spirit or scope thereof and it should be understood that the invention is intended to be limited only as defined in the appended claims.

What we claim is:

1. A compound selected from the group consisting of 8-thiotetrahydroquinolines of the formula

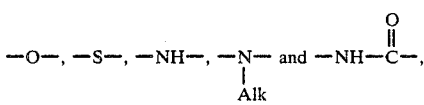

wherein X is selected from the group consisting of $$-O-, -S-, -NH-, -N- \text{ and } -NH-\overset{O}{\overset{\|}{C}}-,$$
$$\phantom{-O-, -S-, -NH-, -N- \text{ and } -NH-}|$$
$$\phantom{-O-, -S-, -NH-, -N- \text{ and } -NH-}\text{Alk}$$

Alk is alkyl of 1 to 6 carbon atoms, R₁ and R₂ are individually selected from the group consisting of hydrogen, phenyl and naphthyl or taken together with the carbon atoms to which they are attached form a phenyl optionally substituted with a member of the group consisting of alkyl, alkoxy and alkylthio of 1 to 6 carbon atoms, halogen,

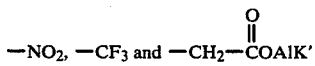

and Alk' is alkyl of 1 to 6 carbon atoms and their non-toxic, pharmaceutically acceptable acid addition salts, 2. A compound of claim 1 wherein $R_1$ and $R_2$ taken together with the carbon atoms to which they are attached form phenyl optionally substituted with at least one member of the group consist ing of alkyl, alkoxy and alkylthio of 1 to 4 carbon atoms, halogen, —$NO_2$, —$CF_3$, —$CH_2COOCH_3$ and —$CH_2COOCH_2$—$CH_3$.

3. A compound of claim 1 wherein X is —S—or —NH—.

4. A compound of claim 1 selected from the group consisting of 8-(2-benzothiazolylthio)-5,6,7,8-tetrahydroquinoline; 8-(6-chloro-1H-benzimidazol-2-ylthio)-5,6,7,8-tetrahydroquinoline; 8-[(5-chloro-2-benzothiazolyl)thio]-5,6,7,8-tetrahydroquinoline; 8-[(6-chloro-2-benzothiazolyl)thio]-5,6,7,8-tetrahydroquinoline; 8-[(6-ethoxy-2-benzothiazolyl)thio]-5,6,7,8-tetrahydroquinoline; 8-[(6-ethylthio-2-benzothiazolyl)thio]-5,6,7,8-tetrahydroquinoline; 8-[(6-nitro-2-benzothiazolyl)thio]-5,6,7,8-tetrahydroquinoline; and 8-(4,5-diphenyl-1H-imidazol-2-ylthio)-5,6,7,8-tetrahydroquinoline, and their non-toxic, pharmaceutically acceptable acid addition salts.

5. An antiallergic composition comprising an antiallergically effective amount of a compound of claim 1 and an inert pharmaceutical carrier 6. A composition of claim 5 wherein in the compound $R_1$ and $R_2$ taken together with the carbon atoms to which they are attached form phenyl optionally substituted with a member of the group consisting of alkyl, alkoxy and alkylthio of 1 to 4 carbon atoms, halogen, —$NO_2$, —$CF_3$, —$CH_2COOCH_3$ and —$CH_2COOCH_2$—$CH_3$.

7. A composition of claim 5 wherein in the compound X is —S—or —NH—.

8. A composition of claim 5 wherein the active compound is selected from the group consisting of 8-(2-benzothiazolylthio)-5,6,7,8-tetrahydroquinoline; 8-(6-chloro-1H-benzimidazol-2-ylthio)-5,6,7,8-tetrahydroquinoline; 8-[(5-chloro-2-benzothiazolyl)thio]-5,6,7,8-tetrahydroquinoline; 8-[(6-chloro-2-benzothiazolyl)thio]-5,6,7,8-tetrahydroquinoline; 8-[(6-ethoxy-2-benzothiazolyl)thio]-5,6,7,8-tetrahydroquinoline; 8-[(6-ethylthio-2-benzothiazolyl)thio]-5,6,7,8-tetrahydroquinoline; 8-[(-6-nitro-2-benzothiazolyl)thio]-5,6,7,8-tetrahydroquinoline; and 8-(4,5-diphenyl-1H-imidazol-2-ylthio)-5,6,7,8-tetrahydroquinoline and their non-toxic, pharmaceutically acceptable acid addition salts.

9. A method of combatting allergies in warm-blooded animals comprising administering to warm-blooded animals an antiallergically effective amount of a compound of claim 1.

10. A method of claim 9 wherein in the compound $R_1$ and $R_2$ taken together with the carbon atoms to which they are attached form phenyl optionally substituted with a member of the group consisting of alkyl, alkoxy and alkylthio of 1 to 4 carbon atoms, halogen, —$NO_2$, —$CF_3$, —$CH_2COOCH_3$ and —$CH_2COOCH_2$—$CH_3$.

11. A method of claim 9 wherein in the compound X is —S—or —NH—.

12. A method of claim 9 wherein the active compound is selected from the group consisting of 8-(2-benzothiazolylthio)-5,6,7,8-tetrahydroquinoline; 8-(6-chloro-1H-benzimidazol-2-ylthio)-5,6,7,8-tetrahydroquinoline; 8-[(5-chloro-2-benzothiazolyl)thio]-5,6,7,8-tetrahydroquinoline; 8-(6-chloro-2-benzothiazolyl)thio]-5,6,7,8-tetrahydroquinoline; 8-[(6-ethoxy-2-benzothiazolyl)thio]-5,6,7,8-tetrahydroquinoline; 8-[(6-ethylthio-2-benzothiazolyl)thio]-5,6,7,8-tetrahydroquinoline; 8-[(6-nitro-2-benzothiazolyl)thio]-5,6,7,8-tetrahydroquinoline; and 8-(4,5-diphenyl-1H-imidazol-2-ylthio)-5,6,7,8-tetrahydroquinoline and their non-toxic, pharmaceutically acceptable acid addition salts.

* * * * *